United States Patent
Ichikawa

(10) Patent No.: US 10,459,010 B2
(45) Date of Patent: Oct. 29, 2019

(54) CURRENT DETECTION ELEMENT INCLUDING A COIL-SHAPED CURRENT DETECTION CONDUCTOR, TRANSMISSION DEVICE, AND ELECTRIC POWER TRANSMISSION SYSTEM

(71) Applicant: MURATA MANUFACTURING CO., LTD., Kyoto-fu (JP)

(72) Inventor: Keiichi Ichikawa, Nagaokakyo (JP)

(73) Assignee: Murata Manufacturing Co., Ltd., Kyoto-fu (JP)

( * ) Notice: Subject to any disclaimer, the term of this patent is extended or adjusted under 35 U.S.C. 154(b) by 102 days.

(21) Appl. No.: 15/715,402

(22) Filed: Sep. 26, 2017

(65) Prior Publication Data
US 2018/0017599 A1    Jan. 18, 2018

Related U.S. Application Data

(63) Continuation of application No. PCT/JP2016/065238, filed on May 24, 2016.

(30) Foreign Application Priority Data

May 28, 2015 (JP) ................. 2015-108391

(51) Int. Cl.
G01R 15/18     (2006.01)
H01F 38/30     (2006.01)
(Continued)

(52) U.S. Cl.
CPC ............ G01R 15/18 (2013.01); G01N 27/04 (2013.01); H01F 27/2804 (2013.01);
(Continued)

(58) Field of Classification Search
CPC .. G01R 15/181; G01R 19/0092; G01R 15/18; G01R 15/185; G01R 19/0084;
(Continued)

(56) References Cited

U.S. PATENT DOCUMENTS 3,153,758 A * 10/1964 Kusters .................. G01R 1/28
                                                                    324/726
4,754,214 A *  6/1988 Bramanti ............... G01N 22/00
                                                                    324/638
(Continued)

FOREIGN PATENT DOCUMENTS

EP    1 553 420 A1    7/2005
JP    H03-084905 A    4/1991
(Continued)

OTHER PUBLICATIONS

International Search Report issued in PCT/JP2016/065238; dated Aug. 2, 2016.
(Continued)

Primary Examiner — Vinh P Nguyen
(74) Attorney, Agent, or Firm — Studebaker & Brackett PC

(57) ABSTRACT

A current detection element includes a laminate where multiple insulator layers are laminated, a main line conductor formed in the laminate, extending in one direction, a coil-shaped current detection conductor that is formed in the laminate and that is magnetically coupled with the main line conductor, and electrostatic shielding conductors that are formed in the laminate, and that are grounded. The electrostatic shielding conductors overlap at least one of the main line conductor and the current detection conductor in plan view from a winding axis direction along a winding axis of the current detection conductor. Accordingly, a current detection element that accurately detects high-frequency AC current flowing through a line, and a transmission device and electric power transmission system having the same, are provided.

11 Claims, 11 Drawing Sheets

(51) Int. Cl.
*H02J 50/12* (2016.01)
*G01N 27/04* (2006.01)
*H01F 27/28* (2006.01)
*H01F 27/36* (2006.01)
*H02J 7/02* (2016.01)

(52) U.S. Cl.
CPC ........... *H01F 27/362* (2013.01); *H01F 38/30* (2013.01); *H02J 50/12* (2016.02); *H01F 2027/2809* (2013.01); *H02J 7/025* (2013.01)

(58) Field of Classification Search
CPC ...... G01R 31/08; G01R 31/086; G01R 31/40; G01R 35/005; G01R 15/207; G01R 15/14; G01R 19/2513; G01R 1/07; G01R 22/00; G01R 31/001; G01R 11/067; G01R 19/25; G01R 21/06; G01R 21/133; G01R 27/2611; G01R 29/24; G01R 31/026; G01R 31/1245; G01R 31/1254; G01R 33/422; G01R 35/04; G01N 29/2406; H01R 4/28; H02G 1/02; H01J 37/321; H01J 37/32697; H01J 37/32935; H01J 37/3299; H04B 3/46; H04B 5/0043; H04B 5/0075
See application file for complete search history.

(56) References Cited

U.S. PATENT DOCUMENTS

| | | | |
|---|---|---|---|
| 5,124,642 A * | 6/1992 | Marx | G01R 15/18 174/139 |
| 6,184,672 B1 * | 2/2001 | Berkcan | G01R 15/181 324/117 R |
| 6,452,413 B1 | 9/2002 | Burghartz | |
| 2015/0241483 A1 * | 8/2015 | Berton | G01R 19/0092 324/126 |

FOREIGN PATENT DOCUMENTS

| | | |
|---|---|---|
| JP | 2004-257964 A | 9/2004 |
| JP | 2007-155597 A | 6/2007 |
| JP | 2015-052470 A | 3/2015 |
| JP | 2015-052471 A | 3/2015 |
| JP | 2015-059838 A | 3/2015 |
| WO | 2015/053246 A1 | 4/2015 |

OTHER PUBLICATIONS

Written Opinion issued in PCT/JP2016/065238; dated Aug. 2, 2016.
International Preliminary Report on Patentability issued in PCT/JP2016/065238; dated Nov. 28, 2017.

* cited by examiner

CURRENT DETECTION ELEMENT INCLUDING A COIL-SHAPED CURRENT DETECTION CONDUCTOR, TRANSMISSION DEVICE, AND ELECTRIC POWER TRANSMISSION SYSTEM

CROSS REFERENCE TO RELATED APPLICATIONS

This application claims benefit of priority to Japanese Patent Application 2015-108391 filed May 28, 2015, and to International Patent Application No. PCT/JP2016/065238 filed May 24, 2016, the entire content of which is incorporated herein by reference.

TECHNICAL FIELD

The present disclosure relates to a current detection element that detects high-frequency AC current flowing through a line, a transmission device, and an electric power transmission system.

BACKGROUND

Japanese Unexamined Patent Application Publication No. 3-84905 describes a DC current sensor for detecting current flowing through a power supply line of an IC. This DC current sensor has a straight-line-shaped DC line connection electrode connected to the power supply line, and a coil-shaped AC line connection electrode, laid out within a magnetic chip where multiple magnetic substance layers are laminated. When current flows to the DC line connection electrode, inductance of the AC line connection electrode changes. This is used to detect DC current on the power supply line.

SUMMARY

Technical Problem

In a case where the DC current sensor described in Japanese Unexamined Patent Application Publication No. 3-84905 is further reduced in size, the distance between the DC line connection electrode and the AC line connection electrode becomes shorter. In this case, capacitance may occur between the electrodes, and the electrodes may be magnetically coupled with each other. DC current is detected in Japanese Unexamined Patent Application Publication No. 3-84905, so this magnetic coupling is not problematic. However, if magnetic coupling occurs between the electrodes in a case of detecting AC current, there is a concern that unwanted noise generated at the DC line connection electrode will flow over to the AC line connection electrode through this capacitance, and accurate current detection cannot be performed.

Accordingly, it is an object of the present disclosure to provide a current detection element that accurately detects high-frequency AC current flowing through a line, and a transmission device and electric power transmission system having the same.

Solution to Problem

A current detection element according to the present disclosure includes an insulator, a main line conductor formed in the insulator, a coil-shaped current detection conductor that is formed in the insulator and that is magnetically coupled with the main line conductor, and an electrostatic shielding conductor that is formed in the insulator, and that is grounded. The electrostatic shielding conductor overlaps at least one of the main line conductor and the current detection conductor in plan view from a winding axis direction along a winding axis of the current detection conductor.

According to this configuration, providing the electrostatic shielding conductor enables the influence that voltage of the main line conductor has on the current detection conductor to be reduced. More specifically, capacitance occurs between the main line conductor and the current detection conductor. Unwanted noise from voltage on the main line conductor flows into the current detection conductor via this capacitance. In a case of providing the electrostatic shielding conductor, unwanted noise (voltage) from the main line conductor is divided by capacitance between the main line conductor and the current detection conductor, and capacitance between the current detection conductor and the electrostatic shielding conductor. Accordingly, even in a case where the voltage of the main line conductor is great, the voltage thereof is divided, so the voltage input to the current detection conductor is smaller in comparison with a case where there is no electrostatic shielding conductor. Accordingly, the influence that the voltage of the main line conductor has on the current detection conductor can be suppressed. As a result, current can be accurately detected even if the voltage of the main line conductor is great.

In the current detection element according to the present disclosure, a configuration may be made where the main line conductor has a shape of a straight line in one direction.

According to this configuration, inductance and resistance value of the main line conductor can be suppressed.

In the current detection element according to the present disclosure, a configuration may be made where the electrostatic shielding conductor has an inter-conductor shielding part formed between the main line conductor and the current detection conductor.

According to this configuration, capacitance can be kept from occurring between the main line conductor and current detection conductor.

In the current detection element according to the present disclosure, a configuration may be made where the current detection element includes two current detection conductors each of which is the current detection conductor, the two current detection conductors are formed having winding axes in the same direction, and the main line conductor is disposed between the two current detection conductors in plan view from the winding axis direction.

According to this configuration, in a case where the two current detection conductors are independent, two current detection results can be obtained. Also, in a case where the two current detection conductors are connected in series, the magnetic coupling between the main line conductor 11 and the current detection conductors can be intensified, and current detection can be performed with good sensitivity. In a case where the two current detection conductors are connected in parallel, the resistance of the current detection conductors can be reduced, and loss can be suppressed.

In the current detection element according to the present disclosure, a configuration may be made where the two current detection conductors are connected in series.

According to this configuration, the magnetic coupling between the main line conductor and the current detection conductors can be intensified, and current detection can be performed with good sensitivity.

In the current detection element according to the present disclosure, a configuration may be made where capacitance occurring between the main line conductor and the electrostatic shielding conductor is smaller than capacitance occurring between the current detection conductor and the electrostatic shielding conductor.

If capacitance occurring between the main line conductor and electrostatic shielding conductor is great, the amount of current flowing form the main line conductor 11 to that capacitance is great, which affects current flowing through the main line conductor. According to the above configuration, the influence on the main line conductor and a circuit connected to the main line conductor can be reduced.

In the current detection element according to the present disclosure, a configuration may be made where the electrostatic shielding conductor has an opening connected to an outer edge of the electrostatic shielding conductor, the opening overlapping at least part of a coil opening of the current detection conductor in plan view from the winding axis direction.

According to this configuration, forming the electrostatic shielding conductor as an open-loop shape can prevent unnecessary magnetic flux from being generated from the electrostatic shielding conductor, and that magnetic flux cancelling out magnetic flux generated from the current detection conductor. Electrostatic shielding of the current detection conductor can be performed by the electrostatic shielding conductor, and leakage of electric field noise can be reduced.

In the current detection element according to the present disclosure, a configuration may be made where the current detection element includes two electrostatic shielding conductors each of which is the electrostatic shielding conductor, and the two electrostatic shielding conductors are formed sandwiching the main line conductor and the current detection conductor therebetween in the winding axis direction.

According to this configuration, the influence that the voltage of the main line conductor has on the current detection conductor can be reduced even further. As a result, current can be accurately detected.

In the current detection element according to the present disclosure, a configuration may be made where the current detection element further includes a grounding mounting electrode provided on a principal surface of the insulator, the current detection conductor is formed with the winding axis thereof intersecting the principal surface of the insulator, and the electrostatic shielding conductor includes a connecting conductor formed within the coil opening of the current detection conductor and connected to the grounding mounting electrode.

According to this configuration, even in a case where part of the electrostatic shielding conductor is to be provided on the opposite side from the principal surface of the insulating member, part can be connected to the grounding mounting electrode provided on the principal surface thereof, via the connecting conductor. The connecting conductor is formed within the coil opening of the current detection conductor, so excess space can be reduced by efficient usage of the opening of the current detection conductor. Consequently, the size of the current detection element can be reduced.

The present disclosure is a transmission device that includes a transmission-side coupling unit that is coupled with a reception-side coupling unit included in a reception device by at least one of an electric field and a magnetic field, and that transmits electric power to the reception device by at least one of magnetic coupling and electric coupling. The transmission device includes a current detection unit that detects current flowing through an electric power transmission line connected to the transmission-side coupling unit. The current detection unit includes an insulator, a main line conductor formed in the insulator, a coil-shaped current detection conductor that is formed in the insulator and that is magnetically coupled with the main line conductor, and an electrostatic shielding conductor that is formed in the insulator, and that is grounded. The electrostatic shielding conductor overlaps at least part of the main line conductor and the current detection conductor in plan view from a winding axis direction along a winding axis of the current detection conductor, and the main line conductor constitutes part of the electric power transmission line.

The present disclosure is an electric power transmission system in which a transmission-side coupling unit included in a transmission device and a reception-side coupling unit included in a reception device are coupled by at least one of an electric field and a magnetic field, and electric power is transmitted from the transmission device to the reception device. The transmission device includes a current detection unit that detects current flowing through an electric power transmission line connected to the transmission-side coupling unit. The current detection unit includes an insulator, a main line conductor formed in the insulator, a coil-shaped current detection conductor that is formed in the insulator and that is magnetically coupled with the main line conductor, and an electrostatic shielding conductor that is formed in the insulator, and that is grounded. The electrostatic shielding conductor overlaps at least part of the main line conductor and the current detection conductor in plan view from a winding axis direction along a winding axis of the current detection conductor, and the main line conductor constitutes part of the electric power transmission line.

According to this configuration, in the transmission device, current flowing through the transmission-side coupling unit can be detected with good sensitivity. Determination of whether or not a reception device has been placed thereupon, and state detection of abnormalities and so forth, can be performed from the magnitude of the detected current, and change in phase.

Advantageous Effects of Disclosure

According to the present disclosure, the influence that the voltage of the main line conductor has on the current detection conductor can be reduced. As a result, current can be accurately detected even if the voltage on the main line conductor is great.

DETAILED DESCRIPTION

Figure 1A:
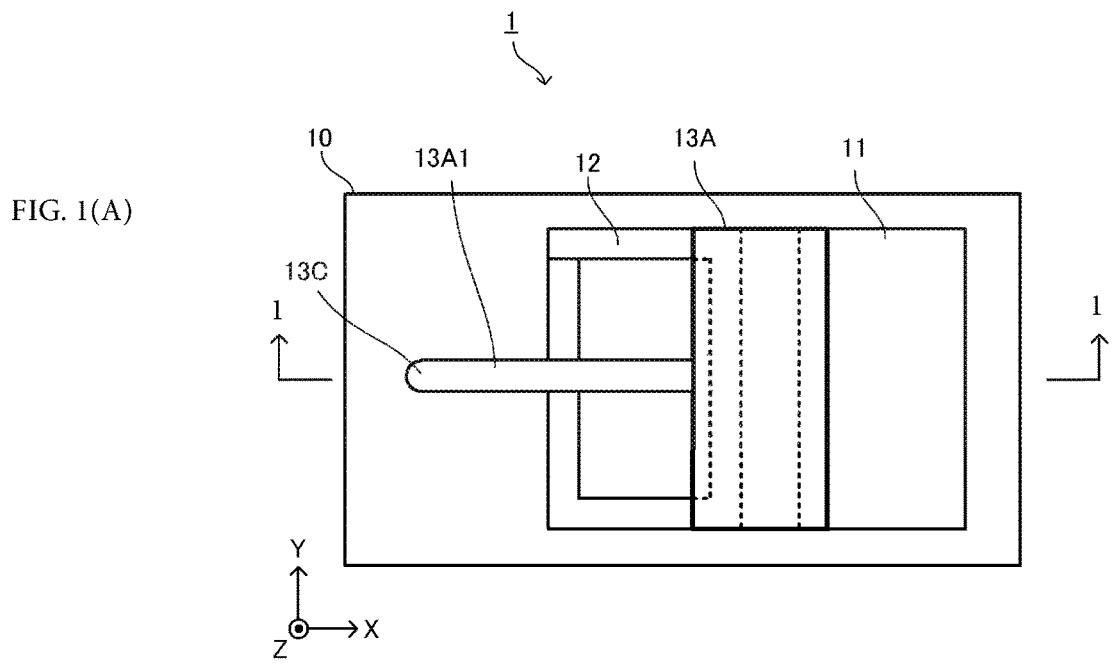
FIG. 1(A) is a plan view of a current detection element according to Embodiment 1.
Figure 1B:
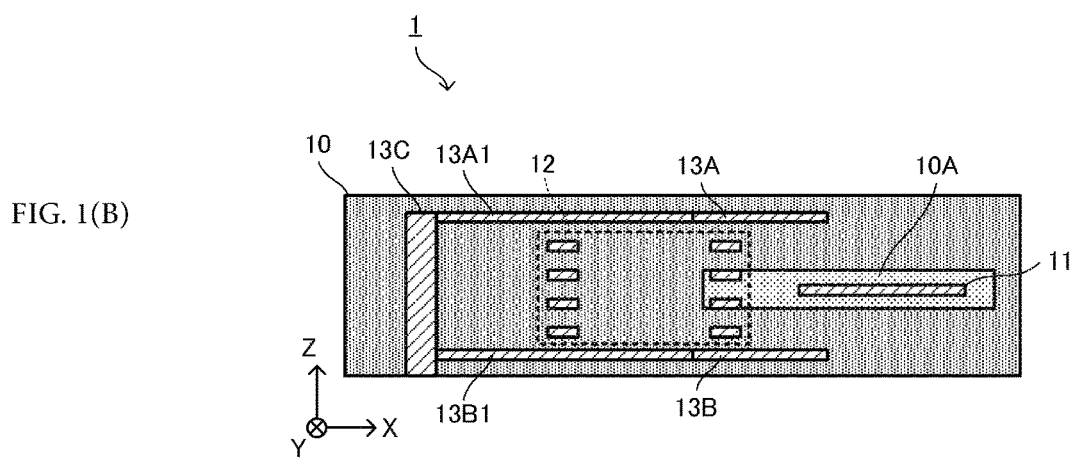
FIG. 1(B) is a cross-section along line 1-1 in FIG. 1(A).

FIG. 1(A) is a plan view of a current detection element according to Embodiment 1, and FIG. 1(B) is a cross-section along line 1-1 in FIG. 1(A). Note that the plan view illustrated in FIG. 1(A) is a transparent view.

A current detection element 1 has a laminate 10. The laminate 10 is formed by laminating multiple insulator layers and sintering. Insulator layers include insulator layers consisting of just magnetic substances such as ferrite or the like, and insulator layers consisting of magnetic substances and non-magnetic substances. A magnetic substance is a ferromagnetic substance, where the relative permeability is $\mu_r > 1$. A non-magnetic substance has a lower permeability than the surrounding magnetic substance, and the relative permeability is $\mu_r = 1$. When these insulator layers are laminated, a high-permeability portion due to the magnetic substance, and a low-permeability portion 10A that has a lower permeability than the surrounding high-permeability portion due to the non-magnetic substance, are formed in the laminate 10. Note that a magnetic substance with a low permeability ($\mu_r \neq 1$, but lower than the permeability of the magnetic substance) may be used instead of the non-magnetic substance. Also, the insulator layers may be non-magnetic layers alone (dielectric ceramic, resin, etc.).

The laminating direction of the laminate 10 is the Z direction. The plane directions of the insulator layers are the X direction and Y direction.

Multiple mounting electrodes (not illustrated) for mounting to a motherboard are formed on one principal surface of the laminate 10. The current detection element 1 is mounted with the principal surface of the laminate 10 on which the mounting electrodes are formed (a surface of the laminate 10 at the negative side in the Z direction. Hereinafter referred to as a lower face) toward the motherboard side. FIG. 1(A) is a plan view viewing the other principal surface that is to the other side of the laminate 10 from the lower face of the laminate 10 in the laminating direction of the laminate 10 (a surface of the laminate 10 at the positive side in the Z direction. Hereinafter referred to as upper face).

A straight-line shaped main line conductor 11 that is long in the Y direction is formed within the low-permeability portion 10A of the laminate 10. Each of both ends of the main line conductor 11 in the longitudinal direction are connected to different mounting electrodes via inter-layer connecting conductors that are not illustrated. The main line conductor 11 is formed in the shape of a straight line, so formation of the main line conductor 11 is easy, and inductance and resistance value of the main line conductor 11 can be reduced.

Although the main line conductor 11 illustrated in FIG. 1 is formed by a conductor pattern printed on one insulator layer, the main line conductor 11 may be formed by conductor patterns being formed on multiple different insulator layers, and these being connected by inter-layer conductors. In this case, the resistance value of the main line conductor 11 can be reduced.

Also, an arrangement may be made where the main line conductor 11 is extended to a side face of the laminate 10 that is parallel to the Z direction, and connected to a mounting electrode via a side wall. In this case, the connecting conductor connecting the main line conductor 11 with the mounting electrode is situated on the outer side of the magnetic substance, so the inductance of the main line conductor 11 and connecting conductor can be further reduced.

A coil-shaped current detection conductor 12 is formed in the laminate 10. The current detection conductor 12 is formed by open-loop-shaped conductors printed on principal surfaces of different insulator layers of the laminate 10 being connected by inter-layer connecting conductors (not illustrated). Also, the winding axis of the current detection conductor 12 is in the Z direction, and formed so as to be partly situated within the low-permeability portion 10A. Further, when viewed in plan view from the Z direction, the current detection conductor 12 is disposed adjacent to the main line conductor 11 across a gap.

Each of both ends of the current detection conductor 12 are connected to different mounting electrodes formed on the lower face of the laminate 10, by inter-layer connecting conductors (not illustrated). The winding direction of the current detection conductor 12 is not restricted in particular.

Plate-shaped electrostatic shielding conductors 13A and 13B are formed in the laminate 10, facing each other in the Z direction. The main line conductor 11 and current detection conductor 12 are interposed between the electrostatic shielding conductors 13A and 13B. The electrostatic shielding conductors 13A and 13B partially overlap the main line conductor 11 and current detection conductor 12 when viewed in plan view from the Z direction. Note that an arrangement may be made where just at least one of the electrostatic shielding conductors 13A and 13B is present.

The electrostatic shielding conductors 13A and 13B are connected to an inter-layer connecting conductor 13C extending in the Z direction via connecting conductors 13A1 and 13B1. The inter-layer connecting conductor 13C is connected to a mounting electrode (not illustrated) formed on the lower face of the laminate 10. This mounting electrode is grounded when the current detection element 1 is mounted onto a board. That is to say, in a case where the current detection element 1 is mounted to a board, the potential of the electrostatic shielding conductors 13A and 13B is ground potential. Ground potential here indicates reference potential of the circuit.

Note that the current detection element 1 is formed such that the distance between the main line conductor 11 and the electrostatic shielding conductors 13A and 13B is longer than the distance between the current detection conductor 12 and the electrostatic shielding conductors 13A and 13B, which will be described later.

When current (high-frequency AC current) flows through the main line conductor 11 in the current detection element 1 having this configuration, magnetic flux is generated. The magnetic flux generated from the main line conductor 11 is linked at the coil opening of the current detection conductor 12. Accordingly, the main line conductor 11 and current detection conductor 12 are magnetically coupled. Induced electromotive force is generated at the current detection conductor 12, and induced current flows in accordance with the induced electromotive force. The current flowing through the main line conductor 11 can be detected by detecting this induced electromotive force or induced current. Note that the magnetic coupling can be intensified due to the low-permeability portion 10A between the main line conductor 11 and the current detection conductor 12, so current detection can be performed with good sensitivity.

In a case where the voltage at the main line conductor 11 is high, there are cases where noise due to the voltage flows into the current detection conductor 12 at this time of current detection, and is superimposed on the output of the current detection conductor 12 as noise, so current detection cannot be performed with good sensitivity. Specifically, parasitic capacitance occurs between the main line conductor 11 and current detection conductor 12. Unwanted noise from the main line conductor 11 flows into the current detection conductor 12 via this capacitance. Accordingly, the electrostatic shielding conductors 13A and 13B are disposed in the present embodiment to prevent unwanted noise from flowing into the current detection conductor 12, thereby raising accuracy of current detection.

Figure 2:
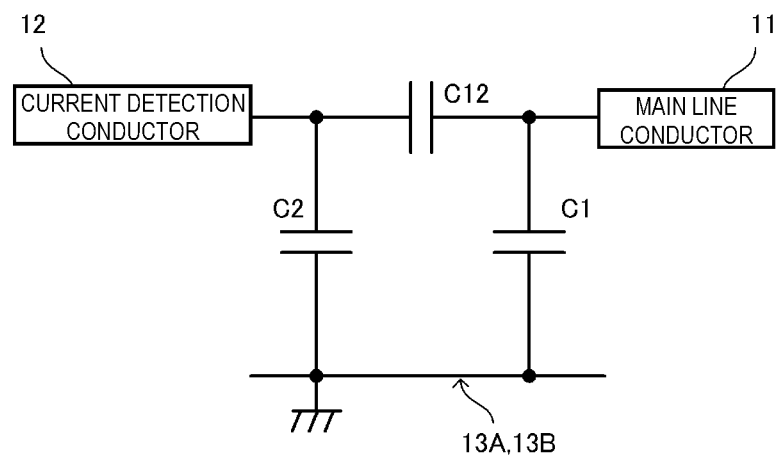
FIG. 2 is a diagram for describing advantages of providing electrostatic shielding conductors.

FIG. 2 is a diagram for explaining advantages of providing the electrostatic shielding conductors 13A and 13B.

Capacitance occurring between the main line conductor and the electrostatic shielding conductors 13A and 13B is represented by C1, capacitance occurring between the current detection conductor 12 and the electrostatic shielding conductors 13A and 13B by C2, and capacitance occurring between the main line conductor 11 and the current detection conductor 12 by C12. In a case where the current detection element 1 is mounted to a board, the potential at the electrostatic shielding conductors 13A and 13B is ground potential, as mentioned earlier.

In the circuit illustrated in FIG. 2, the voltage input to the current detection conductor 12 is divided voltage where the voltage from the main line conductor 11 has been divided at the capacitance C12 and the capacitance C2. Accordingly, even if the voltage at the main line conductor 11 is great, the voltage is divided at the capacitance C12 and the capacitance C2, so a voltage lower than the voltage of the main line conductor 11 is input to the current detection conductor 12. Accordingly, the influence that the voltage of the main line conductor 11 has on the current detection conductor 12 can be reduced. As a result, even if the voltage of the main line conductor 11 is great, little noise voltage is superimposed on the current detection conductor 12, so current can be detected with good sensitivity.

Note that in a case where the capacitance C1 is great, more current flows from the main line conductor 11 to the capacitance C1, which influences the current flowing to the main line conductor 11. Accordingly, the distance between the electrostatic shielding conductors 13A and 13B and the main line conductor 11 is longer than the distance between the electrostatic shielding conductors 13A and 13B and the current detection conductor 12 as described above, so that C2>C1, thereby reducing the influence on the main line conductor 11.

Also, it is possible to reduce the noise voltage superimposed on the current detection conductor 12 by the voltage at the main line conductor 11 by making the distance between the main line conductor 11 and the current detection conductor 12 longer, to make the capacitance C12 smaller. However, in a case where the distance between the main line conductor 11 and current detection conductor 12 is made to be longer, the magnetic coupling between the main line conductor 11 and current detection conductor 12 becomes weaker. In this case, the current detection sensitivity also deteriorates. Accordingly, providing the electrostatic shielding conductors 13A and 13B enables influence that the voltage at the main line conductor 11 has on the current detection conductor 12 can be suppressed without distancing the main line conductor 11 and current detection conductor 12 from each other.

Although the electrostatic shielding conductors 13A and 13B partly overlap each of the main line conductor 11 and current detection conductor 12 in plan view as viewed from the Z direction in the present embodiment, the size of the electrostatic shielding conductors 13A and 13B in plan view can be changed as appropriate. For example, the electrostatic shielding conductors 13A and 13B may overlap the entirety of the main line conductor 11. Also, the electrostatic shielding conductors 13A and 13B may overlap the entirety of the current detection conductor 12. Further, the current detection element 1 may have just one of the electrostatic shielding conductors 13A and 13B.

Note that although the electrostatic shielding conductors 13A and 13B in the present embodiment are plane-like conductors, these may be mesh-like conductors. Although the base for the main line conductor 11, current detection conductor 12, and electrostatic shielding conductors 13A and 13B, is the laminate 10 where multiple insulator layers are laminated in the present embodiment, an article obtained by molding resin or the like may be used as the base instead of a laminate.

Embodiment 2

Figure 3A:
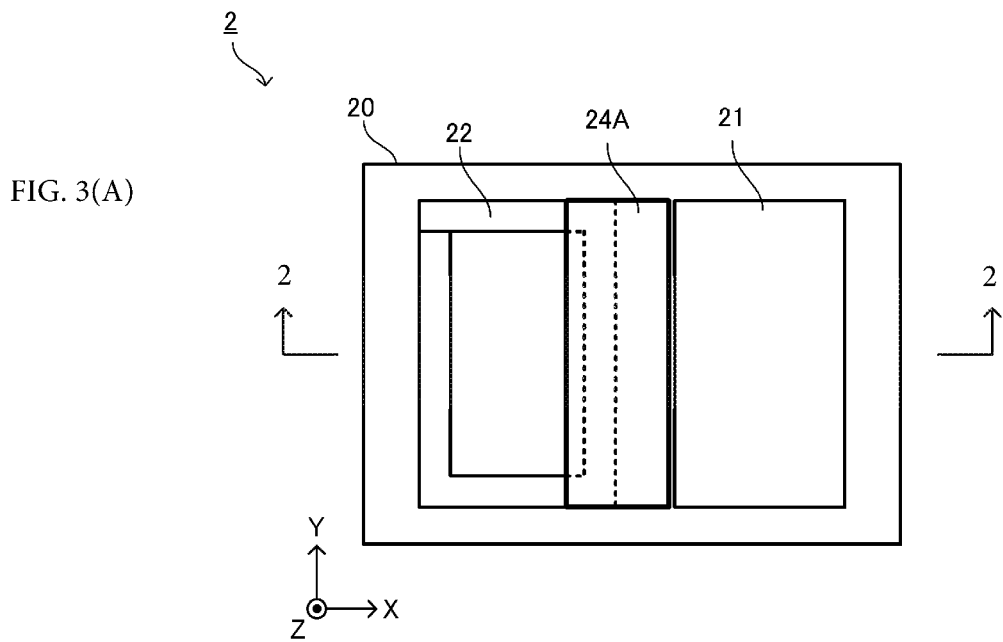
FIG. 3(A) is a plan view of a current detection element according to Embodiment 2.
Figure 3B:
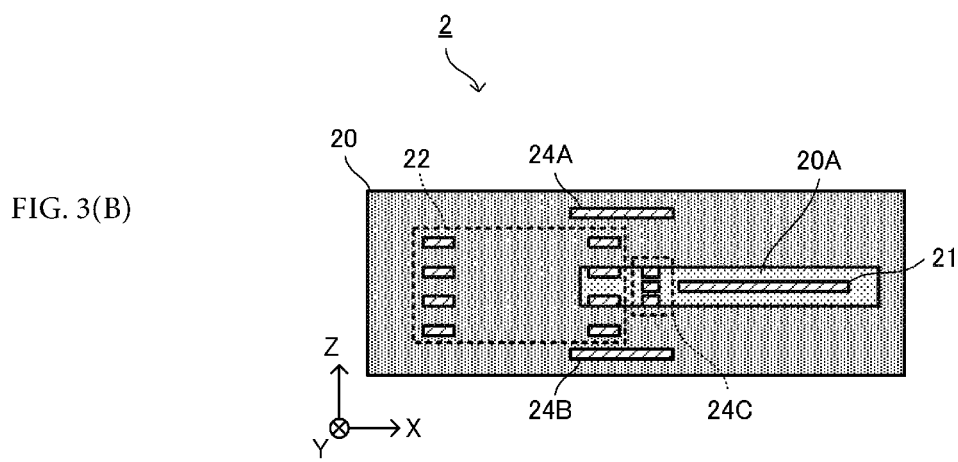
FIG. 3(B) is a cross-section along line 2-2 in FIG. 3(A).

FIG. 3(A) is a plan view of a current detection element according to Embodiment 2, and FIG. 3(B) is a cross-section along line 2-2 in FIG. 3(A). Note that the plan view illustrated in FIG. 3(A) is a transparent view.

The current detection element 2 differs from the current detection element 1 according to Embodiment 1 with regard to the configuration of electrostatic shielding conductors 24A, 24B, and 24C. A laminate 20, main line conductor 21, and current detection conductor 22, are the same as the laminate 10, main line conductor 11, and current detection conductor 12 according to Embodiment 1, so description will be omitted. The laminating direction of the laminate 20 is the Z direction, and the plane directions of the insulator layers are the X direction and Y direction in the present embodiment, in the same way as in Embodiment 1.

Electrostatic shielding conductors 24A and 24B are plate shaped, and face each other in the Z direction. The electrostatic shielding conductors 24A and 24B are formed so that the main line conductor 21 and current detection conductor are interposed therebetween. The electrostatic shielding conductors 24A and 24B overlap part of the current detection conductor 22 in plan view as viewed from the Z direction. The electrostatic shielding conductor 24C is formed in multiple insulator layers of the laminate 20 between the main line conductor 21 and current detection conductor 22. The electrostatic shielding conductors 24A, 24B, and 24C are connected to a grounding mounting electrode formed on the lower face of the laminate 20 via an inter-layer connecting conductor (not illustrated), or the like. The electrostatic shielding conductor 24C is an example of an "inter-conductor shielding part" according to the present disclosure.

In this configuration, the influence that the voltage at the main line conductor 21 has on the current detection conductor 22 can be suppressed by the electrostatic shielding conductors 24A and 24B, in the same way as in Embodiment 1. Providing the electrostatic shielding conductor 24C enables the capacitance generated between the main line conductor 21 and the current detection conductor 22 (capacitance C12 illustrated in FIG. 2) to be reduced. As a result, the influence that the voltage at the main line conductor 21 has on the current detection conductor 22 can be suppressed even further.

Note that although the electrostatic shielding conductors 24A and 24B only overlap the current detection conductor 22 in plan view as viewed from the Z direction, just the main line conductor 21 may be overlapped.

Figure 4A:
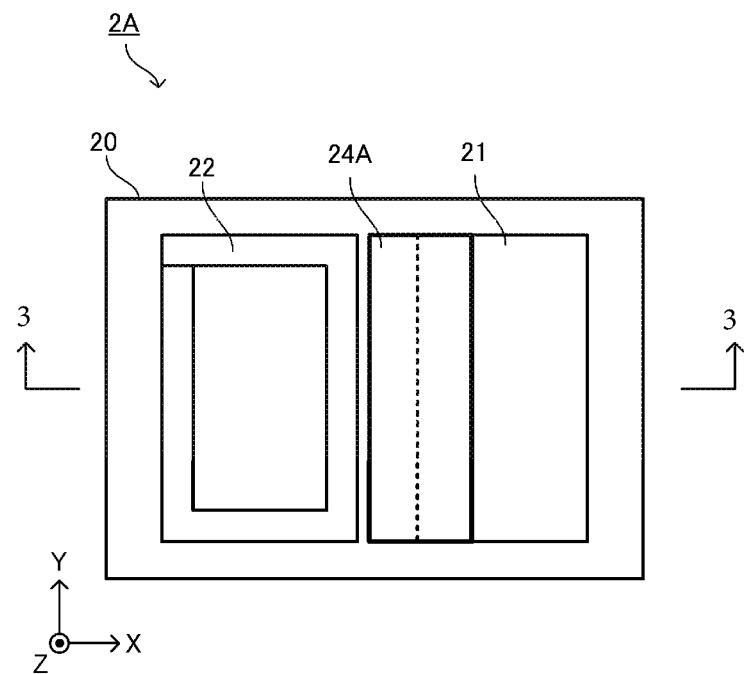
FIG. 4(A) is a plan view of a current detection element according to another example.
Figure 4B:
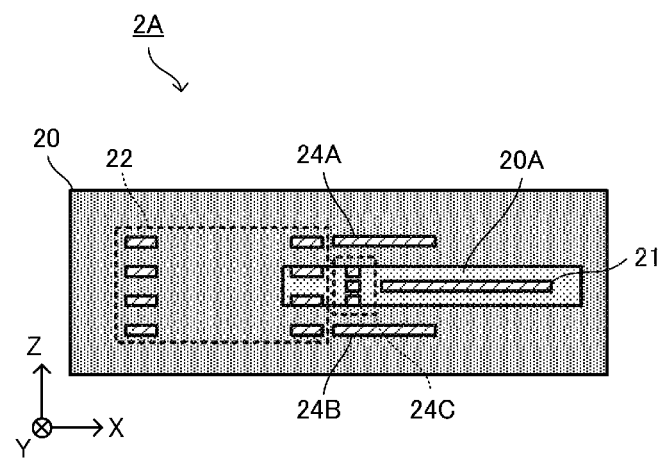
FIG. 4(B) is a cross-section along line 3-3 in FIG. 4(A).

FIG. 4(A) is a plan view of a current detection element 2A according to another example, and FIG. 4(B) is a cross-section along line 3-3 in FIG. 4(A). In the current detection element 2A illustrated in this example, the electrostatic shielding conductors 24A and 24B only overlap part of the main line conductor 21, and do not overlap the current detection conductor 22 in plan view as viewed from the Z direction. This configuration can reduce influence that the voltage at the main line conductor 21 has on the current detection conductor 22 by the electrostatic shielding conductors 24A and 24B, as well. Further, current detection can be performed accurately.

Embodiment 3

Figure 5A:
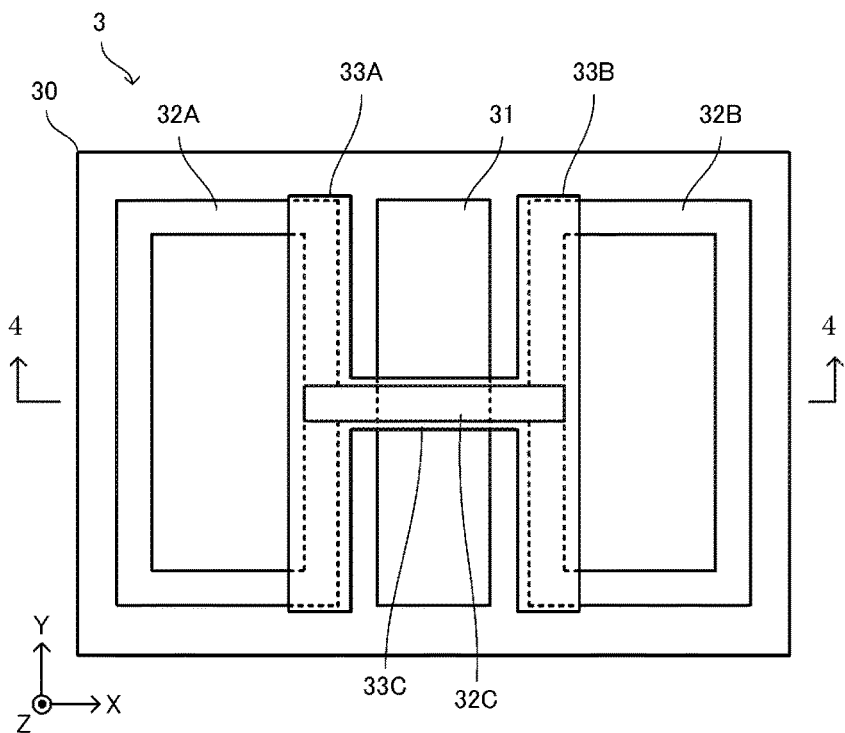
FIG. 5(A) is a plan view of a current detection element according to Embodiment 3.
Figure 5B:
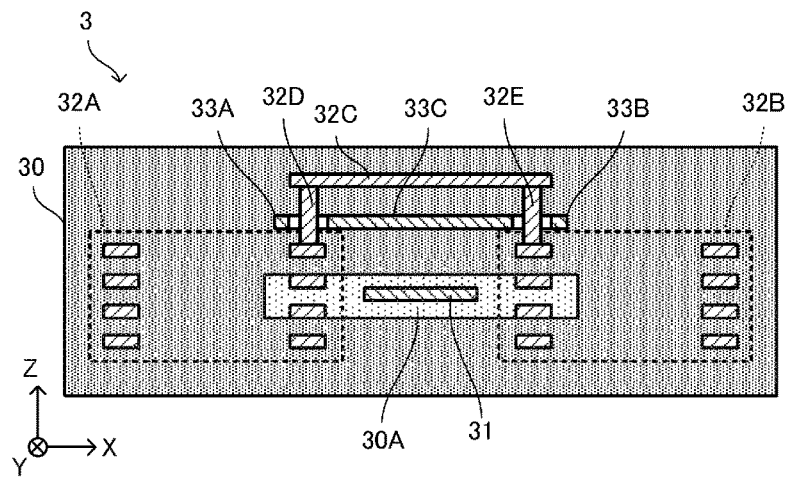
FIG. 5(B) is a cross-section along line 4-4 in FIG. 5(A).

FIG. 5(A) is a plan view of a current detection element according to Embodiment 3, and FIG. 5(B) is a cross-section along line 4-4 in FIG. 5(A). Note that the plan view illustrated in FIG. 5(A) is a transparent view.

The current detection element 3 has a laminate 30. The laminate 30 is of the same configuration as the laminates 10 and according to Embodiments 1 and 2, with a low-permeability portion 30A that has lower permeability than the surroundings being formed at a part in the laminate 30. Note that the laminating direction of the laminate 30 is the Z direction. The plane directions of the insulator layers are the X direction and Y direction.

A main line conductor 31 that is in the form of a straight line and long in the Y direction is formed within the low-permeability portion 30A of the laminate 30. The main line conductor 31 has the same configuration as the main line conductors 11 and 21 in Embodiments 1 and 2.

Coil-shaped current detection conductors 32A and 32B are formed in the laminate 30. The current detection conductors 32A and 32B are formed by open-loop-shaped conductors printed on principal surfaces of different insulator layers of the laminate being connected by inter-layer connecting conductors (not illustrated). The winding axes of the current detection conductors 32A and 32B are in the Z direction, and formed so as to be partly situated within the low-permeability portion 30A. The current detection conductors 32A and 32B are formed so as to sandwich the main line conductor 31 therebetween in plan view as viewed from the Z direction.

One end of each of the current detection conductors 32A and 32B at the lower side (negative side in the Z direction) are connected to mounting electrodes on the lower face of the laminate 30. The current detection conductors 32A and 32B are connected to each other at one end at the upper side via a connecting conductor 32C. In the present embodiment, the current detection conductors 32A and 32B and the connecting conductor 32C is an example of a "current detection conductor" according to the present disclosure.

The connecting conductor 32C is formed spanning the upper side (positive side in the Z direction) of the main line conductor 31. One end of the connecting conductor 32C is connected to the one upper end of the current detection conductor 32A by an inter-layer connecting conductor 32D, and the other end of the connecting conductor 32C is connected to the one upper end of the current detection conductor 32B by an inter-layer connecting conductor 32E. The current detection conductors 32A and 32B form a single coil by being connected in series by the connecting conductor 32C.

When current flows through the main line conductor 31, magnetic flux is generated from the main line conductor 31. The generated magnetic flux is linked at the current detection conductors 32A and 32B. Accordingly, the main line conductor 31 and current detection conductors 32A and 32B are magnetically coupled. Induced electromotive force is generated at the current detection conductors 32A and 32B due to the magnetic coupling, and induced current flows through the current detection conductors 32A and 32B in accordance with the induced electromotive force. The current flowing through the main line conductor 31 can be detected by detecting this induced electromotive force or induced current. In the present embodiment, the current detection conductors 32A and 32B are connected in series, so the magnetic coupling of the main line conductor 31 and the current detection conductors 32A and 32B can be intensified, and current detection can be performed with good sensitivity.

The current detection conductors 32A and 32B connected in series by the connecting conductor 32C are formed such that induced currents flowing therethrough do not cancel each other out. For example, in a case where both of the current detection conductors 32A and 32B are left-handed helixes, the current detection conductors 32A and 32B have the one end of each other at the positive side in the Z direction connected by the connecting conductor 32C. The directions of induced currents generated at the current detection conductors 32A and 32B at this time are each opposite in plan view as viewed from the Z direction. Accordingly, the magnetic coupling of the main line conductor 31 and the current detection conductors 32A and 32B is not weakened.

Note that the structures and way of connection of the current detection conductors 32A and 32B is not restricted to this. The winding directions of the structures and the way of connection of the current detection conductors 32A and 32B can be selected such that the induced currents generated at the current detection conductors 32A and 32B due to the main line conductor 31 and the current detection conductors 32A and 32B being magnetically coupled do not cancel each other out.

The current detection conductors 32A and 32B may also be independent from each other. In this case, two current detection results can be obtained. Further, the two current detection conductors 32A and 32B may be connected in parallel. In this case, the resistance of the current detection conductors 32A and 32B can be reduced, and loss can be suppressed. A configuration may also be made where the current detection conductors 32A and 32B can be switched between a parallel connection and a serial connection by a switching device or the like. Accordingly, switching can be performed to a parallel connection in a case where a great current is flowing through the main line, and to a serial connection where a small current is flowing, for example.

Plate-shaped electrostatic shielding conductors 33A, 33B, and 33C are formed in the laminate 30. The electrostatic shielding conductors 33A and 33B are formed as rectangles that are long in the Y direction. The electrostatic shielding conductors 33A and 33B are also formed sandwiching the main line conductor 31 therebetween, at positions where the electrostatic shielding conductors 33A and 33B overlap part of the current detection conductors 32A and 32B, in plan view as viewed from the Z direction. The electrostatic shielding conductors 33A and 33B further are formed between the current detection conductors 32A and 32B and the connecting conductor 32C in the Z direction.

The electrostatic shielding conductor 33C is formed as a rectangle that is long in the X direction. The electrostatic shielding conductor 33C connects with each of the electrostatic shielding conductors 33A and 33B, with the electrostatic shielding conductors 33A, 33B, and 33C forming a single conductor. The electrostatic shielding conductors 33A, 33B, and 33C are connected to a grounding mounting electrode, formed on the lower face of the laminate 30 via an inter-layer connecting conductor (not illustrated), or the like. The electrostatic shielding conductor 33C is formed between the main line conductor 31 and the connecting conductor 32C in the Z direction. Forming the electrostatic shielding conductor 33C between the main line conductor 31 and the connecting conductor 32C enables capacitance generated between the main line conductor 31 and connecting conductor 32C to be reduced.

Note that the electrostatic shielding conductors 33A and 33B have through holes, and the inter-layer connecting conductors 32D and 32E pass through the through holes. Accordingly, the electrostatic shielding conductors 33A, 33B, and 33C are not in direct contact with the current detection conductors 32A and 32B, and so forth.

This configuration can reduce influence that the voltage at the main line conductor 31 has on the current detection conductors 32A and 32B by the electrostatic shielding conductors 33A and 33B, as well. Influence that the voltage at the main line conductor 31 has on the current detection conductors 32A and 32B can also be reduced by the electrostatic shielding conductor 33C, by reducing capacitance generated between the main line conductor 31 and the connecting conductor 32C. As a result, current detection can be performed accurately.

Embodiment 4

Figure 6A:
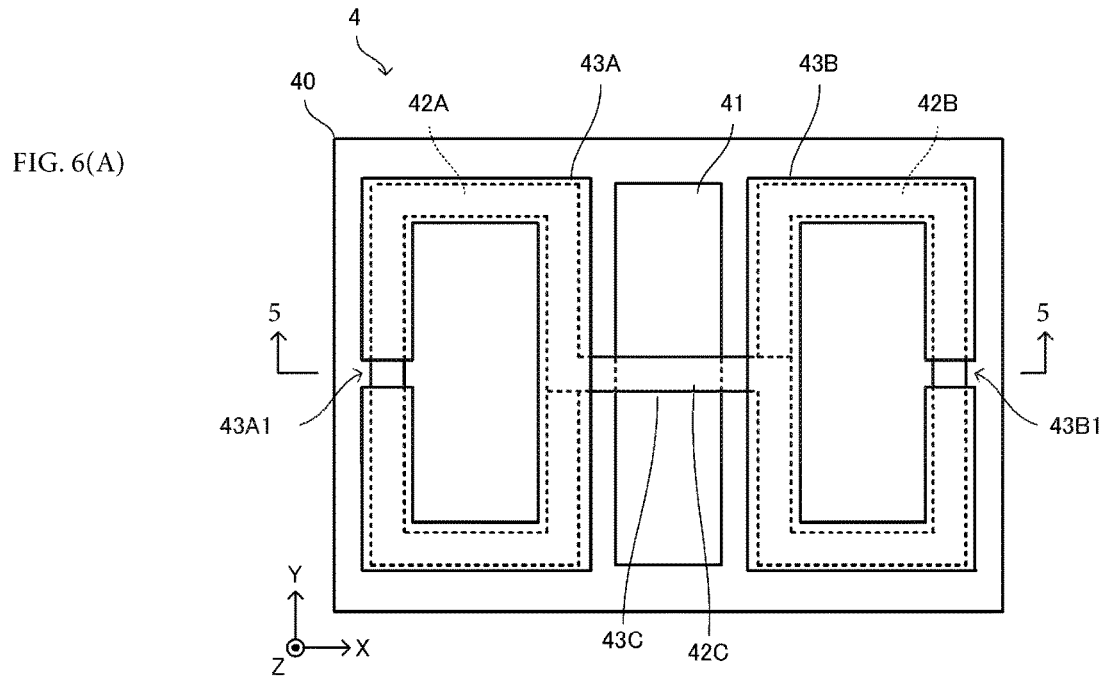
FIG. 6(A) is a plan view of a current detection element according to Embodiment 4.
Figure 6B:
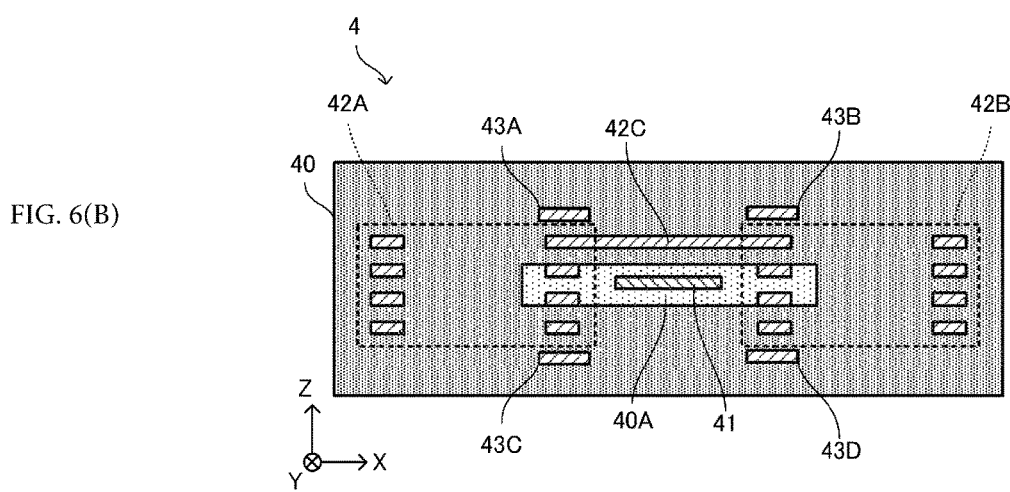
FIG. 6(B) is a cross-section along line 5-5 in FIG. 6(A).

FIG. 6(A) is a plan view of a current detection element according to Embodiment 4, and FIG. 6(B) is a cross-section along line 5-5 in FIG. 6(A). Note that the plan view illustrated in FIG. 6(A) is a transparent view.

The current detection element 4 differs from the current detection element 3 in Embodiment 3 with regard to the configuration of current detection conductors 42A and 42B, and electrostatic shielding conductors 43A, 43B, 43C, and 43D. A laminate 40, a low-permeability portion 40A, and a main line conductor 41 are the same as the laminate 30, low-permeability portion 30A, and main line conductor 31 in Embodiment 3, so description will be omitted. Note that the laminating direction of the laminate 40 is the Z direction, and the plane directions of the insulator layers are the X direction and Y direction in the present embodiment as well, the same as in Embodiment 3.

The current detection conductors 42A and 42B are formed by open-loop-shaped conductors printed on principal surfaces of different insulator layers of the laminate 40 being connected by inter-layer connecting conductors (not illustrated). The winding axes of the current detection conductors 42A and 42B are in the Z direction, and formed so as to be partly situated within the low-permeability portion 40A. The current detection conductors 42A and 42B are further formed so as to sandwich the main line conductor 41 therebetween in plan view as viewed from the Z direction.

One end of each of the current detection conductors 42A and 42B at the negative side in the Z direction are connected to mounting electrodes. The current detection conductors 42A and 42B are connected to each other at one end at the upper side via a connecting conductor 42C. The connecting conductor 42C is formed spanning the main line conductor 41. The current detection conductors 42A and 42B are connected in series by the connecting conductor 42C, thereby forming a single coil.

The electrostatic shielding conductor 43A has the shape of an open loop that has the same diameter as the diameter of the coil opening of the current detection conductor 42A in plan view as viewed from the Z direction, with a notch 43A1 being formed at one part. The electrostatic shielding conductor 43A is formed at a position where the electrostatic shielding conductor 43A overlays the current detection conductor 42A at the positive side of the current detection conductor 42A in the Z direction, in plan view as viewed from the Z direction. The electrostatic shielding conductor 43C has the same shape as the electrostatic shielding conductor 43A, and is formed at the negative side of the current detection conductor 42A in the Z direction, so as to sandwich the current detection conductor 42A between itself and the electrostatic shielding conductor 43A.

The electrostatic shielding conductor 43B has the shape of an open loop that overlays the coil opening of the current detection conductor 42B in plan view as viewed from the Z direction, with a notch 43B1 being formed at one part. That is to say, the electrostatic shielding conductor 43B has an opening that is connected with the outer edge of the electrostatic shielding conductor 43B in plan view. The electrostatic shielding conductor 43B is formed at a position where the electrostatic shielding conductor 43B overlays the current detection conductor 42B at the positive side of the current detection conductor 42B in the Z direction in plan view. The electrostatic shielding conductor 43D has the same shape as the electrostatic shielding conductor 43B, and is formed at the negative side of the current detection conductor 42B in the Z direction, so as to sandwich the current detection conductor 42B between itself and the electrostatic shielding conductor 43B.

The electrostatic shielding conductors 43A, 43B, 43C, and 43D are each connected to grounding mounting electrodes via inter-layer connecting conductors. Note that the respective electrostatic shielding conductors 43A, 43B, 43C, and 43D are shaped as open loops with notches (43A1, 43B1, etc.) being formed. Being formed as open-loop shapes enables generation of magnetic fluxes that would cancel out the magnetic fluxes of the current detection conductors 42A and 42B to be prevented at the electrostatic shielding conductors 43A, 43B, 43C, and 43D.

This configuration can reduce influence that the voltage at the main line conductor 41 has on the current detection conductors 42A and 42B by the electrostatic shielding conductors 43A, 43B, 43C, and 43D, as well. Accordingly, current detection can be performed accurately.

Embodiment 5

Figure 7A:
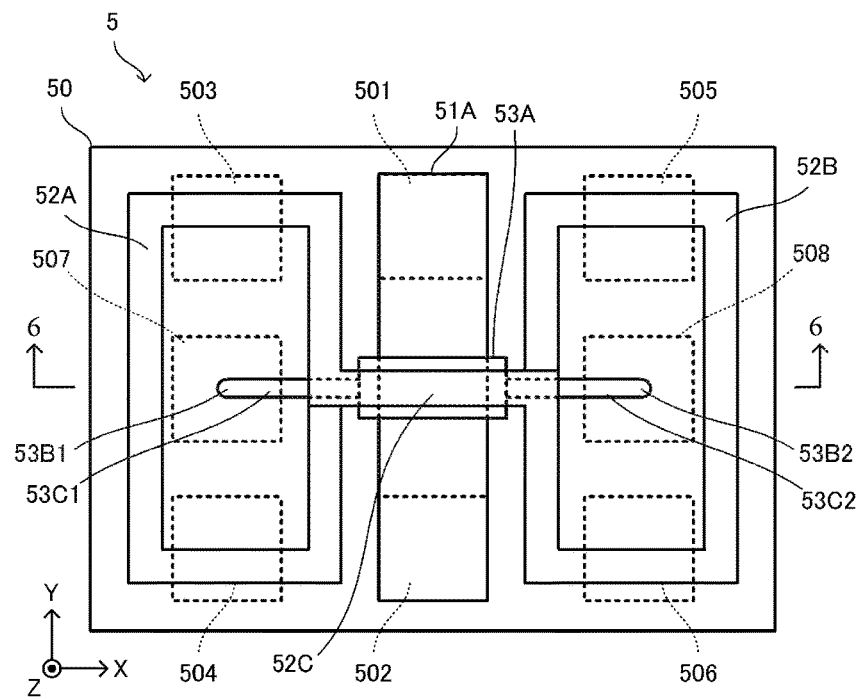
FIG. 7(A) is a plan view of a current detection element according to Embodiment 5.
Figure 7B:
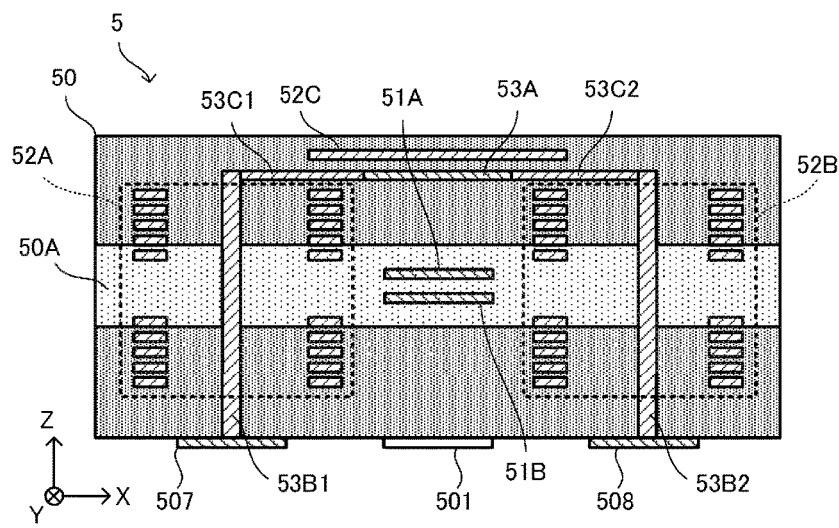
FIG. 7(B) is a cross-section along line 6-6 in FIG. 7(A).

FIG. 7(A) is a plan view of a current detection element according to Embodiment 5, and FIG. 7(B) is a cross-section along line 6-6 in FIG. 7(A). Note that the plan view illustrated in FIG. 7(A) is a transparent view.

A laminate 50 is formed by laminating multiple insulator layers and sintering, in the same way as the laminate according to Embodiment 1. The laminate 50 has a low-permeability portion layer 50A at the middle portion in the laminating direction. The low-permeability portion layer 50A has lower permeability than the insulator layers adjacent above and below in the laminating direction. Note that the thickness of the layers of the laminate 50 is set to be within a range that can tolerate the magnetic flux density of later-described current detection conductors 52A and 52B formed inside.

Straight-line shaped main line conductors 51A and 51B that are long in the Y direction are formed within the low-permeability portion layer 50A of the laminate 50. The main line conductors 51A and 51B have the same shape, and are disposed in parallel so as to be overlaid in the Z direction. Each of both ends of the main line conductors 51A and 51B in the Y direction are connected to mounting electrodes 501 and 502 provided on the mounting face of the laminate 50. This configuration of the two main line conductors 51A and 51B enables impedance of the main line conductor to be reduced. Note that in this example, the mounting electrodes 501 and 502, and the main line conductors 51A and 51B, is an example of a "main line conductor" according to the present disclosure.

The current detection conductors 52A and 52B are formed by open-loop-shaped conductors printed on principal surfaces of different insulator layers of the laminate 50 being connected by inter-layer connecting conductors (not illustrated). The current detection conductors 52A and 52B are formed so as to sandwich the main line conductors 51A and 51B therebetween in plan view as viewed from the Z direction.

One end of the current detection conductor 52A or 52B at the negative side in the Z direction is connected to mounting electrode 503 or 506 by inter-layer connecting conductors. One end of each of the current detection conductors 52A and 52B at the upper face side are connected to each other by a connecting conductor 52C. The connecting conductor 52C is formed spanning the main line conductors 51A and 51B. The current detection conductors 52A and 52B are connected in series by the connecting conductor 52C, thereby forming a single coil.

An electrostatic shielding conductor 53A has a rectangular shape that is long in the X direction in plan view as viewed from the Z direction, and is disposed between the connecting conductor 52C and the main line conductor 51A. Inter-layer connecting conductors 53B1 and 53B2 extending in the Z direction are formed at approximately middle portions of the coil openings of the current detection conductors 52A and 52B. The electrostatic shielding conductor 53A is connected to the inter-layer connecting conductors 53B1 and 53B2 by connecting conductors 53C1 and 53C2. The inter-layer connecting conductors 53B1 and 53B2 are connected to grounding mounting electrodes 507 and 508 provided on the mounting face of the laminate 50.

Note that the mounting electrodes 504 and 505 provided on the mounting face of the laminate 50 are dummy electrodes.

In the present embodiment, the electrostatic shielding conductor 53A, the inter-layer connecting conductors 53B1 and 53B2, and the connecting conductors 53C1 and 53C2, is an example of an "electrostatic shielding conductor" according to the present disclosure.

Thus, by providing the electrostatic shielding conductor 53A between the main line conductors 51A and 51B and the connecting conductor 52C, parasitic capacitance occurring between the main line conductors 51A and 51B and the connecting conductor 52C can be reduced. Thus, unwanted noise from the main line conductors 51A and 51B can be prevented from flowing into the connecting conductor 52C via this capacitance. As a result, the accuracy of current detection by the current detection conductors 52A and 52B can be improved.

Also, the inter-layer connecting conductors 53B1 and 53B2 for setting the potential of the electrostatic shielding conductors 53A and 53B to ground potential are provided at the middle portions of the openings of the current detection conductors 52A and 52B. Such efficient usage of the openings of the current detection conductors 52A and 52B enables excess space to be eliminated. For example, the distance between the current detection conductors 52A and 52B and the main line conductors 51A and 51B in the X direction can be reduced. Consequently, this enables the size of the current detection element 5 to be reduced. Reducing the distance also enables the degree of coupling between the current detection conductors 52A and 52B, and the main line conductors 51A and 51B, to be improved.

Note that the configuration of the electrostatic shielding conductors is not restricted to the configuration in FIG. 7.

Figure 8:
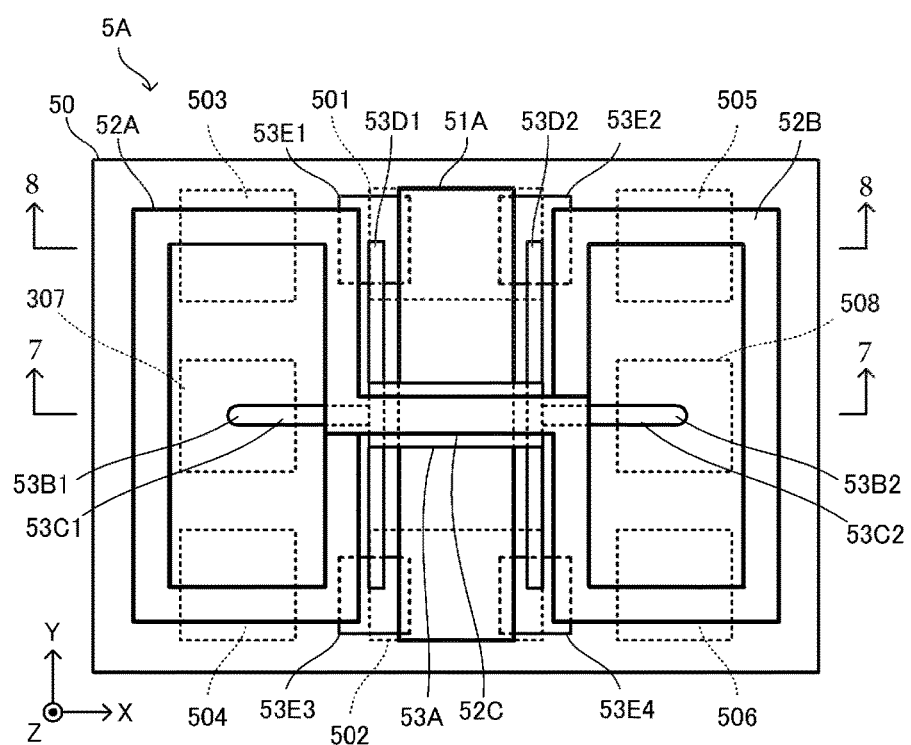
FIG. 8 is a plan view of a current detection element according to another example.
Figure 9A:
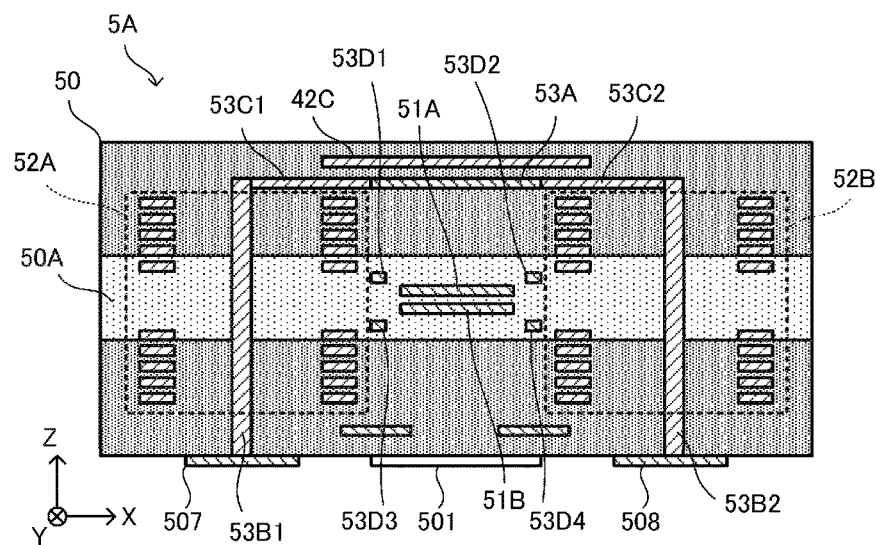
FIG. 9(A) is a cross-section along line 7-7 in FIG. 8.
Figure 9B:
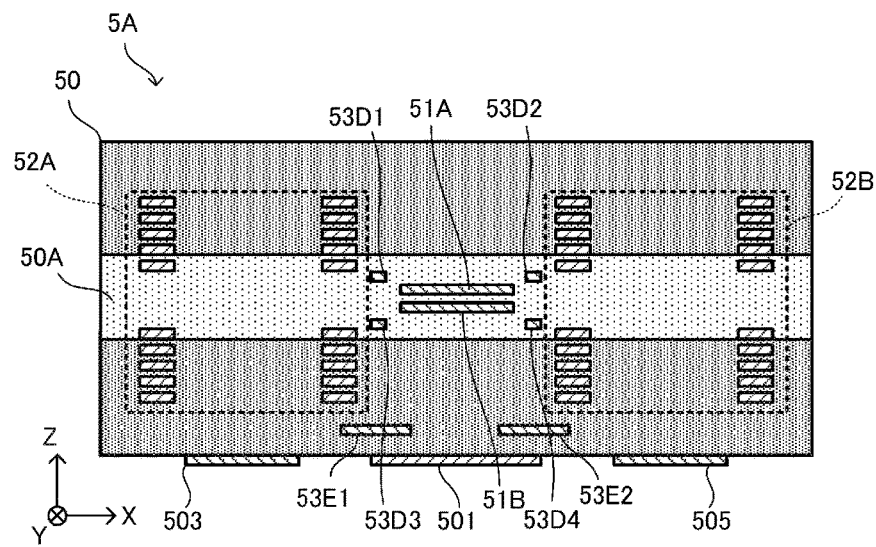
FIG. 9(B) is a cross-section along line 8-8 in FIG. 8.

FIG. 8 is a plan view of a current detection element 5A according to another example. FIG. 9(A) is a cross-section along line 7-7 in FIG. 8, and FIG. 9(B) is a cross-section along line 8-8 in FIG. 8. Note that the plan view illustrated in FIG. 8 is a transparent view.

The current detection element 5A further has electrostatic shielding conductors 53D1, 53D2, 53D3, and 53D4 that extend in the Y direction, besides the electrostatic shielding conductor 53A, the inter-layer connecting conductors 53B1 and 53B2, and connecting conductors 53C1 and 53C2 described in FIG. 7(A) and FIG. 7(B). The electrostatic shielding conductors 53D1 and 53D3 are provided overlapping in the Z direction, and situated between the main line conductors 51A and 51B and the current detection conductor 52A. The electrostatic shielding conductors 53D1 and 53D3 are connected to the inter-layer connecting conductor 53B1 by connecting conductors (not illustrated) extending in the X direction. The electrostatic shielding conductors 53D2 and 53D4 are provided overlapping in the Z direction, and situated between the main line conductors 51A and 51B and the current detection conductor 52B. The electrostatic shielding conductors 53D2 and 53D4 are connected to the inter-layer connecting conductor 53B2 by connecting conductors (omitted from illustration) extending in the X direction.

Parasitic capacitance generated between the main line conductors 51A and 51B, and the current detection conductors 52A and 52B, can be reduced by disposing the electrostatic shielding conductors 53D1, 53D2, 53D3, and 53D4 so as to surround the main line conductors 51A and 51B. Parasitic capacitance can be reduced, so the distance between the main line conductors 51A and 51B and the current detection conductor 52A and 52B can be shortened, and the size of the current detection element 5A can be reduced. Also, shortening the distance enables the degree of coupling between the current detection conductors 52A and 52B and the main line conductors 51A and 51B to be increased.

The current detection element 5A further includes rectangular electrostatic shielding conductors 53E1, 53E2, 53E3, and 53E4. The electrostatic shielding conductors 53E1 and 53E3 are provided at positions overlaying the mounting electrodes 501 and 502 in plan view from the Z direction, and situated between the current detection conductor 52A and the mounting electrodes 501 and 502 in the Z direction. The electrostatic shielding conductors 53E2 and 53E4 are also provided at positions overlaying the mounting electrodes 501 and 502 in plan view from the Z direction, and situated between the current detection conductor 52B and the mounting electrodes 501 and 502 in the Z direction.

Note that the electrostatic shielding conductors 53E1 and 53E3 are connected to the inter-layer connecting conductor 53B1 by connecting conductors (not illustrated) extending in the X direction. The electrostatic shielding conductors 53E2 and 53E4 are connected to the inter-layer connecting conductor 53B2 by connecting conductors (not illustrated) extending in the X direction.

Providing the electrostatic shielding conductors 53E1, 53E2, 53E3, and 53E4 enables parasitic capacitance generated between the mounting electrodes 501 and 502 and the current detection conductors 52A and 52B to be reduced. The main line conductors 51A and 51B are connected to the mounting electrodes 501 and 502. Accordingly, due to the reduction in parasitic capacitance, unwanted noise from the main line conductors 51A and 51B can be prevented from flowing into the current detection conductors 52A and 52B through the parasitic capacitance. As a result, the accuracy of current detection by the current detection conductors 52A and 52B can be increased.

Embodiment 6

This example differs from above-described Embodiments with regard to the structure of the current detection conductors and electrostatic shielding conductors.

Figure 10A:
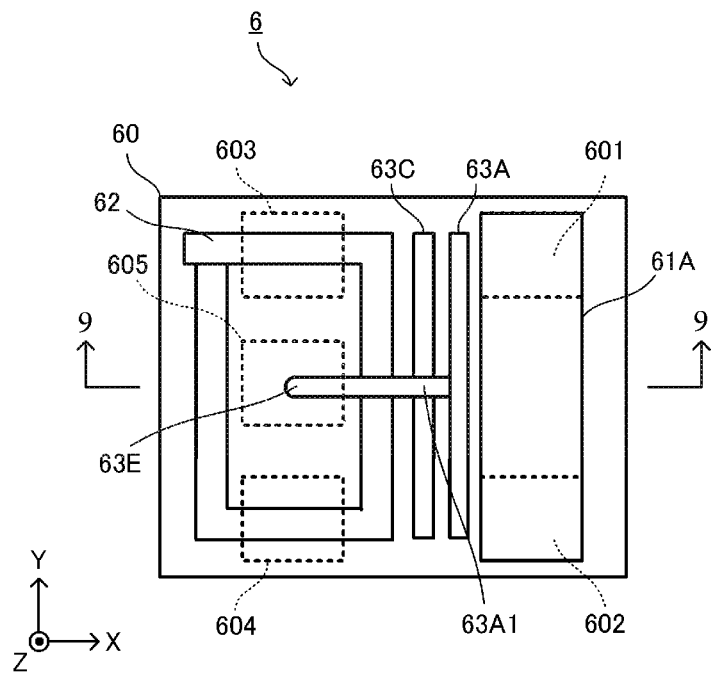
FIG. 10(A) is a plan view of a current detection element according to Embodiment 6.
Figure 10B:
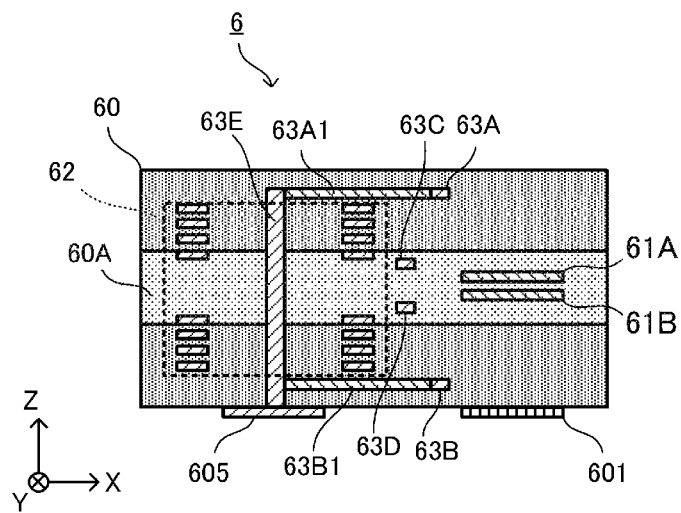
FIG. 10(B) is a cross-section along line 9-9 in FIG. 10(A).

FIG. 10(A) is a plan view of a current detection element 6 according to Embodiment 6, and FIG. 10(B) is a cross-section along line 9-9 in FIG. 10(A). Note that the plan view illustrated in FIG. 10(A) is a transparent view.

A laminate 60 is formed by laminating multiple insulator layers and sintering, in the same way as the laminate according to Embodiment 5. The laminate 60 has a low-permeability portion layer 60A at the middle portion in the laminating direction. Straight-line shaped main line conductors 61A and 61B that are long in the Y direction are formed within the low-permeability portion layer 60A.

The main line conductors 61A and 61B have the same shape, and are disposed in parallel so as to be overlaid in the Z direction. Each of both ends of the main line conductors 61A and 61B are connected to mounting electrodes 601 and 602 provided on the mounting face of the laminate 60. Configuring the main line conductor of the two main line conductors 61A and 61B enables impedance of the main line conductor to be reduced.

A current detection conductor 62 is formed by open-loop-shaped conductors printed on principal surfaces of different insulator layers of the laminate 60 being connected by inter-layer connecting conductors (not illustrated), in the same way as the current detection conductor 52A according to Embodiment 5. The current detection conductor 62 is formed in parallel to the main line conductors 61A and 61B along the Y direction, in plan view as viewed from the Z direction.

One end of the current detection conductor 62 at the positive side in the Z direction is connected to a mounting electrode 603 by an inter-layer connecting conductor. One end of the current detection conductor 62 at the negative side is connected to a mounting electrode 604 by an inter-layer connecting conductor.

Electrostatic shielding conductors 63A, 63B, 63C, and 63D have rectangular shapes which are long in the Y direction in plan view as viewed from the Z direction, and are disposed between the main line conductors 61A and 61B, and the current detection conductor 62. The inter-layer connecting conductors 63A and 63B are overlaid in the Z direction. An inter-layer connecting conductor 63E that extends in the Z direction is formed at an approximately middle portion of the coil opening of the current detection conductor 62. The electrostatic shielding conductors 63A and 63B are connected to the inter-layer connecting conductor 63E by connecting conductors 63A1 and 63B1. The inter-layer connecting conductor 63E is connected to a grounding mounting electrode 605 provided on the mounting face of the laminate 60. The connecting conductors 63A1 and 63B1 are part of the inter-layer connecting conductors 63A and 63B, partially overlapping the current detection conductor 62, and forming electrostatic capacitance between coils and electrostatic shielding conductors.

The electrostatic shielding conductors 63C and 63D are overlaid in the Z direction. The electrostatic shielding conductors 63C and 63D are connected to the inter-layer connecting conductor 63E by connecting conductors that are not illustrated, in the same way as the main line conductors 61A and 61B.

The electrostatic shielding conductors 63A, 63B, 63C, and 63D preferably are arrayed so as to confine electrostatic noise emitted from the main line conductors 61A and 61B. Specifically, the electrostatic shielding conductors 63A and 63B are disposed at the outer side (positive side and negative side) of the electrostatic shielding conductors 63C and 63D in the Z direction, and are situated closer to the side of the main line conductors 61A and 61B than the electrostatic shielding conductors 63C and 63D, without overlapping the electrostatic shielding conductors 63C and 63D in the Z direction. Note that the electrostatic shielding conductors 63A, 63B, 63C, and 63D may overlap.

This configuration can reduce influence that the voltage at the main line conductors 61A and 61B has on the current detection conductor 62, as well, by the electrostatic shielding conductors 63A, 63B, 63C, and 63D reducing capacitance generated between the main line conductors 61A and 61B and the current detection conductor 62. As a result, current detection can be performed accurately.

Also, disposing the inter-layer connecting conductor 63E at the approximately middle portion of the coil opening of the current detection conductor 62 enables the distance between the main line conductors 61A and 61B and the current detection conductor 62 to be shortened, so the current detection element 6 can be reduced in size.

Note that above-described Embodiments 1 through 6 can be combined as appropriate.

Embodiment 7

In this example, an electric power transmission system having the current detection element 1 described in Embodiment 1 will be described.

Figure 11:
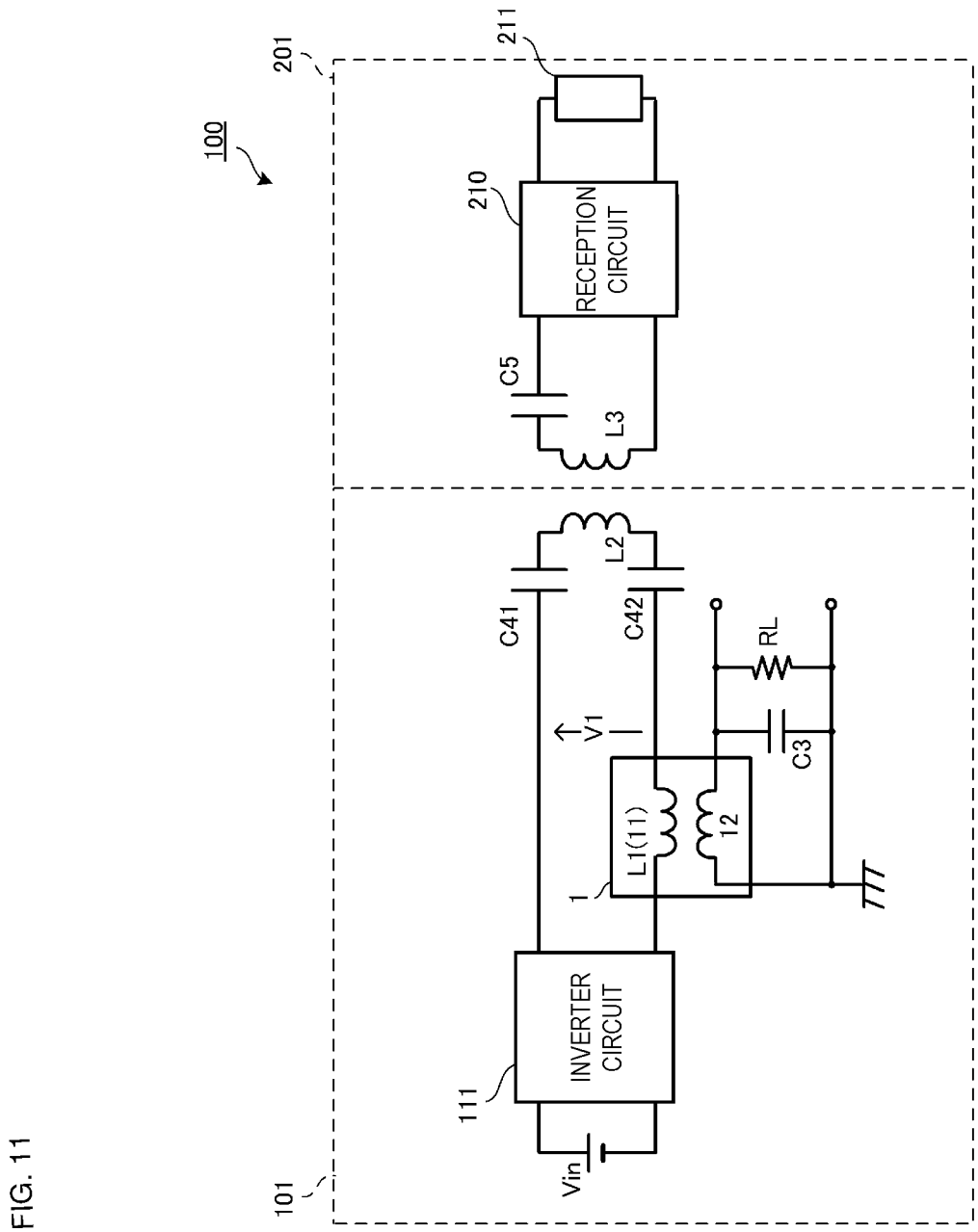
FIG. 11 is a circuit diagram of an electric power transmission system according to Embodiment 7.

FIG. 11 is a circuit diagram of an electric power transmission system 100 according to Embodiment 7.

An electric power transmission system 100 has a transmission device 101 and a reception device 201. The electric power transmission system 100 transmits power from the transmission device 101 to the reception device 201 by magnetic coupling.

The reception device 201 has a load circuit 211. The load circuit 211 includes a charging circuit and a secondary battery. The secondary battery may be detachably mounted to the reception device 201. The reception device 201 is a mobile electronic device, for example, having the secondary battery. Examples of a mobile electronic device include cellular phones, PDAs (Personal Digital Assistant), portable music players, laptop PCs, digital cameras, and so forth. The transmission device 101 is a charging stand for charging the secondary battery of the reception device 201 placed thereupon.

The transmission device 101 has a DC power source Vin that outputs DC voltage. The DC power source Vin is an AC adapter connected to a commercial electric power source. An inverter circuit 111 that converts DC voltage in to AC voltage is connected to the DC power source Vin. A resonance circuit made up of capacitors C41 and C42, and a coil L2 is connected to the output side of the inverter circuit 111. The coil L2 is an example of a "transmission-side coupling unit" according to the present disclosure.

A current detection element 1 is provided between the inverter circuit 111 and the resonance circuit. The main line conductor 11 of the current detection element 1 is part of a power transmission line between the inverter circuit 111 and the resonance circuit. This current detection element 1 is mounted to a motherboard that is not illustrated, and is connected to a capacitor C3 and a load RL.

An inductor L1 in the drawing is the inductance component of the main line conductor 11. When current flows through the inductor L1 and induced current flows through the current detection conductor 12, detecting the voltage at both ends of the load RL enables the current flowing through the main line conductor 11, i.e., the current flowing between the inverter circuit 111 and the resonance circuit (hereinafter, also referred to as transmission current), to be detected. The capacitor C3 is connected to the current detection conductor 12 in parallel, but may be connected in series.

The reception device 201 has a capacitor C5 and a coil L3 that constitute a resonance circuit. Electric power is transmitted from the transmission device 101 to the reception device 201 by the coils L2 and L3 being magnetically coupled. The resonance circuit of this reception device 201 is set to the same resonance frequency as the resonance circuit of the transmission device 101. Setting the resonance frequencies of the resonance circuits of the transmission device 101 and reception device 201 to be the same enables efficient electric power transmission to be performed. The coil L3 is an example of a "reception-side coupling unit" according to the present disclosure.

A reception circuit 210 is connected to the resonance circuit of the reception device 201. The reception circuit 210 rectifies and smoothes voltage induced at the coil L3. The reception circuit 210 also converts the rectified and smoothed voltage into a stabilized predetermined voltage, and supplies to the load circuit 211.

This electric power transmission system 100 can detect impedance when viewing the reception device 201 side from the inverter circuit 111, by detecting the transmission current of the transmission device 101 and input voltage V1 to the resonance circuit of the transmission device 101. Detecting the impedance enables whether or not the reception device 201 has been placed on the transmission device 101 to be detected, for example. In a case where the reception device 201 is placed on the transmission device 101, the resonance circuits of the transmission device 101 and reception device 201 are coupled, exhibiting a frequency peak due to complex resonance. Detecting frequency characteristics of the impedance, and detecting whether or not there is a frequency peak, enables determination of whether the reception device 201 has been placed.

Using the current detection element 1 for detecting transmission current at the transmission device 101 also keeps the size of the device from being large.

Even in a case of only detecting transmission current of the transmission device 101 using the current detection element 1, determination of whether or not a reception device 201 has been placed thereupon, and state detection of abnormalities and so forth, can be performed from the magnitude of the detected current, and change in phase.

Although the current detection element 1 described in Embodiment 1 is used in the electric power transmission system 100, the current detection elements described in Embodiments 2 through 6 may be used. Although the electric power transmission system 100 has been described as a system where the transmission device 101 and reception device 201 are magnetically coupled, this may be a system where the transmission device 101 and reception device 201 are electrically coupled. Further, the current detection elements described in Embodiments 1 through 6 may be used in the reception device 201.

The invention claimed is:

1. A current detection element, comprising:
an insulator;
a main line conductor formed in the insulator;
a coil-shaped current detection conductor formed in the insulator and magnetically coupled with the main line conductor; and
a plate-shaped electrostatic shielding conductor formed inside the insulator, and being grounded, wherein
the electrostatic shielding conductor overlaps at least one of the main line conductor and the current detection conductor in plan view from a winding axis direction along a winding axis of the current detection conductor.

2. The current detection element according to claim 1, wherein
the main line conductor has a shape of a straight line in one direction.

3. The current detection element according to claim 1, wherein
the electrostatic shielding conductor has an inter-conductor shielding part formed between the main line conductor and the current detection conductor.

4. The current detection element according to claim 1, wherein
the current detection element includes two current detection conductors each of which is the current detection conductor,
the two current detection conductors are formed having winding axes in a same direction, and
the main line conductor is disposed between the two current detection conductors in plan view from the winding axis direction.

5. The current detection element according to claim 4, wherein
the two current detection conductors are connected in series.

6. The current detection element according to claim 1, wherein
capacitance occurring between the main line conductor and the electrostatic shielding conductor is smaller than capacitance occurring between the current detection conductor and the electrostatic shielding conductor.

7. The current detection element according to claim 1, wherein
the electrostatic shielding conductor has an opening connected to an outer edge of the electrostatic shielding conductor, the opening overlapping at least part of a coil opening of the current detection conductor in plan view from the winding axis direction.

8. The current detection element according to claim 1, wherein
the current detection element includes two electrostatic shielding conductors each of which is the electrostatic shielding conductor, and
the two electrostatic shielding conductors are formed sandwiching the main line conductor and the current detection conductor between the two electrostatic shielding conductors in the winding axis direction.

9. The current detection element according to claim 1, further comprising
a grounding mounting electrode provided on a principal surface of the insulator, wherein
the current detection conductor is formed with the winding axis thereof intersecting the principal surface of the insulator, and
the electrostatic shielding conductor includes a connecting conductor formed within the coil opening of the current detection conductor and connected to the grounding mounting electrode.

10. A transmission device that includes a transmission-side coupling unit coupled with a reception-side coupling unit included in a reception device by at least one of an electric field and a magnetic field, and transmits electric power to the reception device by at least one of magnetic coupling and electric coupling, the transmission device comprising:
a current detection unit detecting current flowing through an electric power transmission line connected to the transmission-side coupling unit,
wherein the current detection unit includes
an insulator,
a main line conductor formed in the insulator,
a coil-shaped current detection conductor that is formed in the insulator and that is magnetically coupled with the main line conductor, and
an electrostatic shielding conductor formed inside the insulator, and that is grounded,
the electrostatic shielding conductor overlaps at least one of the main line conductor and the current detection conductor in plan view from a winding axis direction along a winding axis of the current detection conductor, and
the main line conductor constitutes part of the electric power transmission line.

11. An electric power transmission system comprising
a transmission-side coupling unit included in a transmission device and a reception-side coupling unit included in a reception device are coupled by at least one of an electric field and a magnetic field, and electric power is transmitted from the transmission device to the reception device,
the transmission device including
a current detection unit detecting current flowing through an electric power transmission line connected to the transmission-side coupling unit,
the current detection unit including
an insulator,
a main line conductor formed in the insulator,
a coil-shaped current detection conductor formed in the insulator and being magnetically coupled with the main line conductor, and
an electrostatic shielding conductor formed inside the insulator, and being grounded, wherein
the electrostatic shielding conductor overlaps at least one of the main line conductor and the current detection conductor in plan view from a winding axis direction along a winding axis of the current detection conductor, and
the main line conductor constitutes part of the electric power transmission line.

* * * * *